US009482675B1

(12) United States Patent
Lovell et al.

(10) Patent No.: US 9,482,675 B1
(45) Date of Patent: Nov. 1, 2016

(54) METHODS AND SYSTEMS FOR PROGNOSIS AND DIAGNOSIS OF BRAIN DAMAGE

(71) Applicant: University of Kentucky Research Foundation, Lexington, KY (US)

(72) Inventors: Mark A. Lovell, Mt. Vernon, KY (US); Bert C. Lynn, Nicholasville, KY (US); Melissa A. Bradley-Whitman, Richmond, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/449,093

(22) Filed: Jul. 31, 2014

Related U.S. Application Data

(60) Provisional application No. 61/860,645, filed on Jul. 31, 2013.

(51) Int. Cl.
*G01N 33/68* (2006.01)
(52) U.S. Cl.
CPC ...... *G01N 33/6872* (2013.01); *G01N 33/6893* (2013.01); *G01N 2333/4727* (2013.01); *G01N 2800/2871* (2013.01)
(58) Field of Classification Search
None
See application file for complete search history.

(56) References Cited

U.S. PATENT DOCUMENTS

| | | | | |
|---|---|---|---|---|
| 5,409,664 A * | 4/1995 | Allen | ............ | G01N 33/521 422/424 |
| 6,673,628 B2 * | 1/2004 | Freitag et al. | ............ | 436/514 |
| 7,097,983 B2 * | 8/2006 | Markovsky et al. | ............ | 435/7.1 |
| 7,145,025 B2 * | 12/2006 | Lockwood et al. | ............ | 549/473 |
| 8,535,617 B2 * | 9/2013 | MacDonald | ............ | G01N 33/491 422/420 |
| 2008/0131881 A1 * | 6/2008 | Ladenson et al. | ............ | 435/6 |

OTHER PUBLICATIONS

Richter et al. (Neuroscience 2000 vol. 96, p. 121-129.*
Lee et al. (Clinical Chem. 2008 vol. 54, p. 1617-1623.*
Li, C. et al., Structural Analysis of $Mg^{2+}$ and $Ca^{2+}$ Binding, Myristoylation, and Dimerization of the Neuronal Calcium Sensor and Visinin-like Protein 1 (VILIP-1), The Journal of Biological Chemistry, 286(8): 6354-6366 (2011).
Santa Cruz Biotechnology, Inc., VILIP-1 (K-25): sc-130827, Product Insert, 1 page. URL: www.scbt.com (Retrieved May 12, 2016).
Santa Cruz Biotechnology, Inc., VILIP-1 (PL-A2): sc-134402, Product Insert, 1 page. URL: www.scbt.com (Retrieved May 12, 2016).

* cited by examiner

*Primary Examiner* — Jacob Cheu
(74) *Attorney, Agent, or Firm* — Choate, Hall & Stewart LLP; Brenda Herschbach Jarrell; Michael L. Vetter

(57) ABSTRACT

The presently-disclosed subject matter includes methods and devices for diagnosing, prognosing, and treating brain damage in a subject, including brain damage caused by stroke or a traumatic brain injury (TBI). The methods can comprise providing a sample obtained from the subject, exposing the sample to an antibody selective for a visinin-like protein, detecting the presence of a complex that includes the antibody and the visinin-like protein, and diagnosing and/or prognosing the subject as having brain damage if there is the presence of the complex. Embodied methods can also comprise administering a treatment for brain damage if the subject includes the presence of the visinin-like protein.

33 Claims, 7 Drawing Sheets

METHODS AND SYSTEMS FOR PROGNOSIS AND DIAGNOSIS OF BRAIN DAMAGE

RELATED APPLICATIONS

This application claims priority from U.S. Provisional Patent Application No. 61/860,645, filed Jul. 31, 2013, the entire disclosure of which is incorporated herein by this reference.

TECHNICAL FIELD

The presently-disclosed subject matter relates to methods and systems for prognosis, diagnosis, and treatment of brain damage in a subject. In particular, the presently-disclosed subject matter relates to methods and systems for prognosing, diagnosing, and treating brain damage that include measuring levels of visinin-like family proteins in a biological sample obtained from a subject.

INTRODUCTION

Traumatic brain injury (TBI) is a significant civilian and military hearth concern. Brain injury can exist in individuals who experience concussive or sub-concussive blows to the head, and has particular relevance to athletic and military activities. Without reliable diagnostics that can determine whether a blow to the head affected the brain, athletes and soldiers can return to their sport or to combat and be exposed to additional injuries which may be associated with chronic and progressive symptoms and neuropathologic damage. Similarly, about 795,000 Americans suffer a stroke each year, and stoke is a leading cause of serious long-term disability. Ischemic strokes, due to blocked blood vessels in the brain, account for about 87% of all strokes.

Current diagnostic and prognostic tools used for evaluation of TBI and stroke remain limited particularly for in field (i.e., pre-hospital) evaluation. Central to the clinical diagnosis of TBI is the use of non-contrast computer tomography (CT) and magnetic resonance imaging (MRI). Non-contrast CT is generally the initial test for diagnosis of TBI because of its availability at most healthcare facilities. Although CT is sensitive in the identification of acute hemorrhage and fracture associated with severe injury, it is relatively insensitive in the identification of diffuse injury associated with milder TBI. Also, CT scans often appear to be normal after the onset of an ischemic stroke and may remain normal for hours after the event. MRI is capable of detecting hematomas, small contusions, and ischemic events not captured by CT, but it is relatively insensitive to diffuse axonal injury and may not be feasible in all situations.

Furthermore, the time delay associated with current diagnostic approaches for stroke patients limits the time during which thrombolytics (tissue plasminogen activator; t-PA) may be administered. Administration of t-PA improves neurologic outcomes in patients with ischemic stroke, but the therapeutic window can be less than 6 hours after the event and can be as few as 2 or 3 hours post ischemia. Because of the potential detrimental effects of use oft-PA in patients with a small hemorrhagic stroke, the lack of a diagnostic that can quickly differentiate between hemorrhagic and ischemic stroke is associated with underuse of fibrinolytic treatment.

Determination of the Glasgow Coma Scale (GCS) is also used to diagnose the degree of brain injury. Patients with mild TBI generally have no penetrating injuries of the head or other organs, experience less than 30 minutes of lost or altered consciousness, may demonstrate post-injury amnesia that lasts more than 24 hours, and generally demonstrate GCS scores of 14 or 15. Therefore, mild TBI is difficult to diagnose because mild TBI can present limited injury and only subtle changes in GCS scores. Patients with moderate TBI generally have a loss of consciousness that lasts greater than 30 minutes, have post injury amnesia, and generally demonstrate GCS scores of 9 to 12. On the other hand, patients with severe TBI, which typically include victims of poly-trauma, are relatively easier to diagnose when compared to patients having mild and moderate injuries.

Because of difficulties associated with clinical diagnosis of mild and moderate TBI and stroke, others have attempted to develop biochemical and surrogate markers of TBI that can be measured in circulating fluids, diagnose the extent of injury, and define the anatomical and cellular pathology associated with injury. Current biomarkers of TBI are classified by their pathophysiological role and include molecules involved in neuroinflammation, glial activation, neuron dysfunction/degeneration, and markers of oxidative stress. Known biomarkers include creatine kinase (CK), glial fibrillary protein (GFAP), lactate dehydrogenase (LDH), myelin basic protein (MBP), neuron specific enolase (NSE), $S100\beta$, and markers of neuroinflammation.

However, known biomarker have limited capabilities For instance, even though known biomarkers may identify subjects having experienced a stroke from normal subjects, known biomarkers are not capable of delineating between ischemic stroke patients and patients having experienced a hemorrhagic stroke, seizure, migraine, syncope, hypoglycemia, and the like. Furthermore, although some biomarkers have been identified as potentially being useful for characterizing brain damage, most known biomarkers are quantified using time-consuming techniques, such as enzyme linked immunoassays (ELISAs) that can take as long as 24 hours to complete. Therefore, known techniques provide limited information on a subject only after an optimal time period for treatment has passed.

Hence, there remains a need for a biomarker that can be used for the diagnosis and prognosis of brain damage. There also remains a need for systems that can be used to identify and measure biomarkers in a sample collected from a subject within a clinically relevant time period.

BRIEF DESCRIPTION OF THE DRAWINGS

The novel features of the presently-disclosed subject matter are set forth with particularity in the appended claims. A better understanding of the features and advantages of the presently-disclosed subject matter will be obtained by reference to the following detailed description that sets forth illustrative embodiments, in which the principles of the invention are used, and the accompanying drawings of which:

DESCRIPTION OF EXEMPLARY EMBODIMENTS

Figure 1:
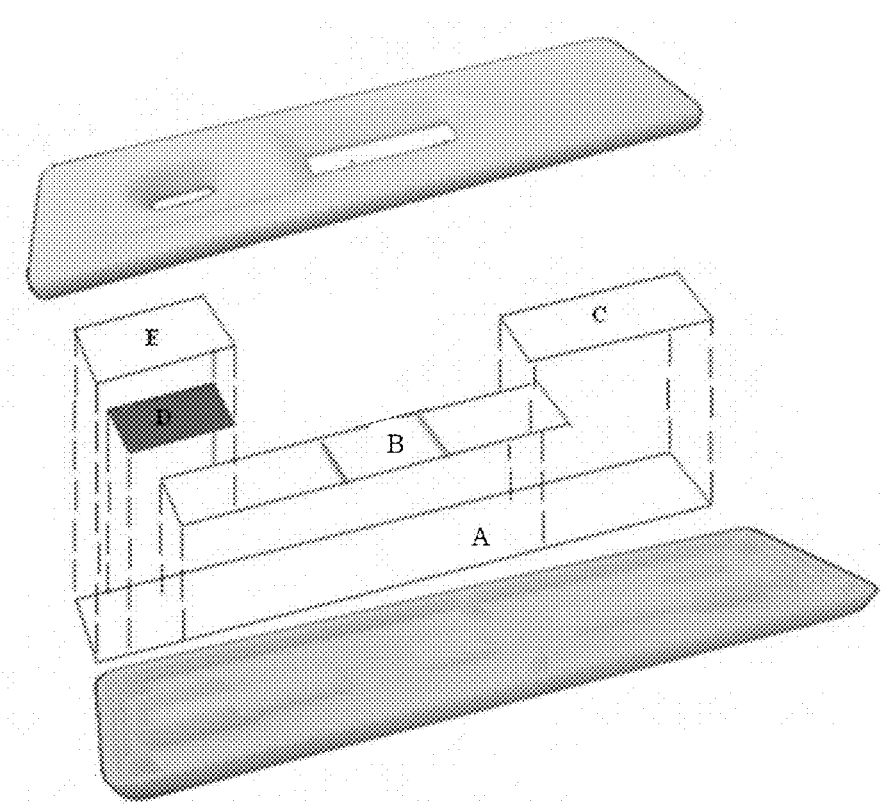
FIG. 1 includes a schematic showing an embodiment of a lateral flow device (LFD) comprising a laminate backing (A), a detection portion (B), a wicking portion (C), a conjugate portion (D), and a sample portion (E), wherein a VILIP-1 K-25 antibody is deposited as a stripe left of 'B', Goat Serum is deposited as a stripe right of 'B', and conjugate that includes nanogold beads labeled with VILIP-1 PL-A2 is illustrated as a shaded area on 'D'.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to methods and systems for diagnosing, prognosing, and/or treating brain damage, including brain damage caused by a stroke and/or a traumatic brain injury (TBI). The present inventors have identified biomarkers that can effectively diagnose and prognose such brain damage. In some instances, the biomarkers of TBI or stroke be based on substrates that are relevant and/or specific to the central nervous system and should provide information about injury mechanisms.

In some instances, the biomarkers be measurable in accessible biological fluids, such as cerebrospinal fluid and blood, and should correlate with the severity of injury and resulting functional deficits. Additionally, exemplary biomarkers have high sensitivity for identification of subjects (i.e., high positive identification), high specificity (i.e., low false positive identifications), and have an appearance profile that follows neuronal/glial injury. In this regard, the present inventors have found that visinin-like proteins (VILIPs) can serve as biomarkers for brain damage.

Diagnosis and Prognosis

The presently-disclosed subject includes methods for diagnosing and/or prognosing brain damage in a subject. Exemplary methods include providing a biological sample obtained from the subject, and subsequently determining a presence of a visinin-like protein in the sample obtained from the subject, the presence of the visinin-like protein indicating that the subject has brain damage. The terms "biological sample" and "sample" are used interchangeably herein to generally refer to a sample that is intended to be subjected to qualitative and/or quantitative measurements to determine whether there is an absence, presence, and/or particular concentration of a component. In some instances the sample includes a circulating fluid, and can include a fluid that circulates within the central nervous system. Exemplary types of biological samples include serum, blood, plasma, cerebrospinal fluid, and the like. The sample may or may not include cells from the subject. Depending on the type of sample obtained for a particular method, any suitable known method can be used to obtain the sample from the subject. The volume of a sample is also not particularly limited, and is about 10 µL to about 1,000 mL in some of the presently-disclosed embodiments.

The term "subject" is not particularly limited, and is inclusive of a vertebrates, such as mammals. The term "subject" includes human and veterinary subjects. Thus, the subject of the herein disclosed methods can be a human, non-human primate, horse, pig, rabbit, dog, sheep, goat, cow, cat, guinea pig, rodent, or the like. The term does not denote a particular age or sex. Thus, adult and newborn subjects, as well as fetuses, whether male or female, are intended to be covered.

The terms "diagnosing," "diagnosis," and the like as used herein refer to methods by which the skilled artisan can estimate and even determine whether or not a subject is suffering from a given disease or condition. Along with diagnosis, "prognosis," "prognosing," and the like are also an area of great concern and interest, and can refer to predicting a clinical outcome (with or without medical treatment), selecting an appropriate treatment (or whether treatment would be effective), or monitoring a current treatment and potentially changing the treatment, based on the presence of a visinin-like protein. The terms "diagnose" and "prognosis" can refer to the ability to determine or predict the course or outcome of a condition with up to 100% accuracy, or predict that a given course or outcome is more or less likely to occur. In certain embodiments, a diagnosis or prognosis is indicative of an about 10%, about 20%, about 30%, about 40%, about 50%, about 60%, about 70%, about 80%, or about 90% chance that the subject has brain damage. If an accurate diagnosis and/or prognosis can be made, appropriate therapy, and in some instances less severe therapy or more effective therapy, for the subject can be chosen. In some embodiments of the presently-disclosed subject matter, a method includes identifying a subject as having brain damage, possible due to TBI or a stroke, if a sample obtained from the subject includes a presence of a visinin-like protein.

In the various methods and system described herein, the visinin-like protein can be selected from the group consisting of VILIP-1, VILIP-2, VILIP-3, hippocalcin, neurocalin delta, and combinations thereof. The terms "polypeptide", "protein", and "peptide", which are used interchangeably herein, refer to a polymer of the protein amino acids regardless of its size or function. The terms "protein", "polypeptide", and "peptide" are used interchangeably herein to also refer to a gene product, homologs, orthologs, paralogs, fragments, any protease derived peptide (fragment), and other equivalents, variants, and analogs of a polymer of amino acids.

In general, calcium balance is maintained in the central nervous system by either Ca buffering or Ca sensing proteins. As mentioned above, the visinin-like protein family represents a specific subfamily of brain associated $Ca^{2+}$-sensors that include VILIP-1, VILIP-2, VILIP-3, hippocalcin, and neurocalin delta. These proteins possess 4 EF-hand $Ca^{2+}$-binding moieties that, upon $Ca^{2+}$ binding, lead to regulation of cyclic nucleotide levels, modulation of voltage gated $Ca^{2+}$ and A type $K^+$ channels, transcriptional repression, kinase modulation, and neurotransmitter release.

For example, VILIP-1 in neurons undergoes a $Ca^{2+}$-dependent association with the plasma membrane or Golgi membranes and has modulatory effects on signaling of cAMP and cGMP. In addition, VILIP-1 modulates activity of guanyl cyclase B through clathrin-dependent receptor cycling and plays a role in regulation of gene expression by binding double stranded RNA. In human brain, VILIP-1 protein has been demonstrated in the prefrontal, cingulate, insular and temporal cortices, putamen, nucleus accumbens but not caudate. In the hippocampus, VILIP-1 is present in a subset of pyramidal neurons in CA1 and CA4 but is not observed in CA2 or CA3. Immunostaining of VILIP-1 in amygdala and hypothalamus is considerably weaker than in hippocampus, whereas intense staining is observed in the cerebellum and in vestibular and trigeminal neurons of the brainstem. VILIP-1 in a rat model of ischemic stroke can be elevated at both the mRNA and protein levels at 24 hour post-injury.

The step of determining the presence of a visinin-like protein is also not particularly limited. In some embodiments the presence of a visinin-like protein can be determined via an enzyme-linked immunosorbent assay (ELISA). In other embodiments the detecting step is performed via a novel lateral flow device that comprises one or more antibodies that are specific for the visinin-like protein, as described further below. Thus, the determining step can include detecting a measurable presence of a visinin-like protein in a substance.

In some embodiments the presence of a visinin-like protein is established if it is determined that the sample includes any measurable amount of the visinin-like protein. In other embodiments the presence of a visinin-like protein is established only if the visinin-like protein is present at a particular concentration and/or range of concentrations. In some embodiments the presence of a visinin-like protein is established if the visinin-like protein is present at concentration of 100 ng/ml or more, 200 ng/ml or more, 300 ng/ml or more, 400 ng/ml or more, 500 ng/ml or more, 600 ng/ml or more, 700 ng/ml or more, 800 ng/ml or more, 900 ng/ml or more, 1,000 ng/ml or more, 2,000 ng/ml or more, 3,000 ng/ml or more, 4,000 ng/ml or more, 5,000 ng/ml or more, 6,000 ng/ml or more, 7,000 ng/ml or more, 8,000 ng/ml or more, 9,000 ng/ml or more, or 10,000 ng/ml or more. In yet other embodiments, as described herein, the concentration of a visinin-like protein can indicate the disease or condition that has or is causing brain damage in a subject.

For example, the present methods for diagnosing and/or prognosing may be used for any brain damage. Types of brain damage that can be diagnosed and/or prognosed with the present methods include, but is not limited to, brain damage caused by a traumatic brain injury (TBI), including mild, moderate, or severe TBI, a stroke, including hemorrhagic stroke or ischemic stroke, a seizure, a migraine, a syncope, and the like. In some embodiments the brain damage can include brain damage due to neuronal damage, hypoxic damage, or both. Thus, the present methods can provide a relatively simple and noninvasive way to identify brain damage caused by a wide range of diseases, conditions, and events for a variety of subjects. In some embodiments the subject includes a premature infant, and the brain damage being diagnosed, prognosed, and/or treated can include neuronal damage, hypoxic damage, and combinations thereof.

In this regard, embodiments of the present methods can be used to determine the severity of brain damage, and optionally can determine the severity of the brain damage as a function of time. For example, embodiments may be able to categorize a TBI as being mild, moderate, or severe based on the concentration of a visinin-like protein in a sample. Thus, in some embodiments the present methods are performed on a subject known or suspected as having a TBI, and in some embodiments is performed about 1 minute to about 24 hours after an event that caused or is suspected of having caused TBI. In some embodiments, a concentration of at least about 200 ng/ml of a visinin-like protein (e.g., VILIP-1) in a sample obtained from a subject one hour post injury indicates that the subject has experienced mild TBI, and for some subjects a concentration of at least about 500 ng/ml of the visinin-like protein-1 one hour post injury indicates that the subject has experienced moderate TBI. In some embodiments where a sample is obtained from a subject three hours post injury, a concentration of about 200 ng/ml to about 800 ng/ml of a visinin-like protein in the sample indicates that the subject experienced a mild TBI, and in other embodiments a concentration of about 800 ng/ml or more of a visinin-like protein in the sample indicates that the subject experienced moderate TBI.

Other embodiments of the present methods can categorize a stroke as being either ischemic or hemorrhagic and/or can categorize the stroke as being mild, moderate, or severe based on concentration of a visinin-like protein present in a sample. In some embodiments a subject can be diagnosed has having experienced an ischemic stroke if the subject exhibits a presence of a visinin-like protein at a concentration that is below a concentration of visinin-like protein expressed in subjects with TBI, including mild TBI, and hemorrhagic stroke. On the other hand, in some embodiments a subject can be diagnosed has having experienced an hemorrhagic stroke if the subject exhibits a presence of a visinin-like protein at a concentration that is approximately equal to or above a concentration of visinin-like protein expressed in subjects with mild TBI.

In specific embodiments the presence of the visinin-like protein at a concentration of about 100 ng/ml to a concentration of about 400 ng/ml in the sample is indicative of ischemic stroke, whereas the presence of the visinin-like protein in excess of about 700 ng/ml in the sample is indicative hemorrhagic stroke. In some embodiments the present methods are performed on subjects known or suspected to have experienced a stroke. In yet other specific embodiments, wherein the subject is a human known or suspected of having experienced a stroke, a presence of the visinin-like protein below about 5,000 ng/ml in a sample obtained from the subject is indicative of ischemic stroke, and a presence of the visinin-like protein above about 5,000 ng/ml in a sample obtained from the subject is indicative of hemorrhagic stroke. In some instances the methods are performed about 1 minute to about 24 hours after the known or suspected stroke in order to provide a clinically relevant diagnosis and/or prognosis.

Additionally, embodiments of the methods and systems described herein can diagnose and/or prognose a subject with brain damage and/or a particular type of brain damage relatively quickly by determining the presence of a visinin-like protein in a sample collected from a subject. The relatively rapid diagnosis and/or prognosis can permit relevant treatments to be administered to a subject in need soon after the occurrence of brain damage, potentially increasing the effectiveness of the administered treatment. For example, in the case of subjects believed to have potentially have suffered a stroke, it can be beneficial to delineate whether the subject has had an ischemic stroke or a hemorrhagic stroke as soon as possible, and in some instances within two hours of the event believed to have been a stroke. Generally, outcomes are superior if treatment can be administered for an ischemic stroke within this early time frame. Generally, treatment for ischemic stroke (e.g., thrombolytic treatment) cannot be administered until one is diagnosed with ischemic stroke, particularly if there is a risk that the subject might otherwise have a TBI or hemorrhagic stroke.

In some embodiments a determination regarding the presence of a visinin-like protein can be made in about 15 minutes or less following obtaining a sample. Regardless of the time required to make such a determination, embodiments of the presently-disclosed methods can provide a diagnosis and/or prognosis in less than about 24 hours, in less than about 6 hours, in less than about 4 hours, in less than about 3 hours, in less than about 2 hours, and in less than about 1 hour following obtaining a sample. In specific embodiments, the present methods and systems can provide a diagnosis and/or prognosis within about 1 to about 30 minutes, or within about 1 to about 15 minutes. This characteristic of embodied methods can be beneficial because visinin-like protein levels can be altered in blood as soon as 1 hour following TBI or ischemic stroke.

In certain embodiments of the presently-disclosed subject matter, a method for diagnosing and/or prognosing brain damage in a subject is provided, wherein the method comprises providing a biological sample obtained from the subject, exposing the sample to an antibody that is selective for a visinin-like protein, detecting the presence of a complex that includes the antibody and the visinin-like protein, and diagnosing and/or prognosing the subject as having brain damage if there is a presence of the complex. The terms "selective for," "selectivity," and the like are used herein to refer to a characteristic of a molecule that preferentially and/or exclusively binds a target molecule. Selectivity can be imparted by the charge, conformation, and/or functional groups of the selective molecule. It will be understood that certain antibodies can selectively bind to target proteins.

Alternatively or additionally, in some embodiments the antibody utilized in the present methods is provided as a conjugate that includes the antibody that is selective for the visinin-like protein and a detection probe. Subsequently, the detecting step includes detecting the presence of a complex that includes the visinin-like protein and the conjugate, which itself includes the antibody conjugated to the detection probe. Detection probes may be selected from those known in the art, including fluorescent compounds, radioactive compounds, nanobeads, visual labels, or combinations thereof. In some embodiments the nanobeads are nanogold beads.

In other embodiments of the present methods for the diagnosis and/or prognosis of brain damage in a subject, the methods can comprise providing a biological sample obtained from the subject, determining a presence of two or more visinin-like proteins in the subject, and diagnosing and/or prognosing the subject as having brain damage if there is the presence of the two or more visinin-like proteins. The two or more visinin-like proteins can be selected from VILIP-1, VILIP-2, VILIP-3, hippocalcin, neurocalin delta, and combinations thereof. In some embodiments at least one of the two or more visinin-like proteins includes VILIP-1.

Treatment

The presently-disclosed subject matter also provides methods for treating brain damage in a subject. Exemplary methods can comprise a step of providing a biological sample obtained from the subject, a step of determining a presence of a visinin-like protein in the subject, wherein the presence of the visinin-like protein indicates that the subject has brain damage, and a step of administering a treatment for brain damage if the subject includes the presence of the visinin-like protein. Accordingly, some embodiments can comprise a step of treating brain damage if the subject is diagnosed and/or prognosed as having brain damage.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another therapy directed toward the improvement of the associated disease, pathological condition, or disorder.

The term "administering" is not particularly limited, and refers to any method of providing a composition and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

In some embodiments the subject is diagnosed and/or prognosed with a certain type of brain damage so that an appropriate treatment can be administered. For example, some embodiments of the present treatment methods comprise administering to the subject a treatment for TBI, hemorrhagic stroke, or ischemic stroke if the subject is diagnosed with, respectively, TBI, hemorrhagic stroke, or ischemic stroke. In some embodiments the treatment for ischemic stroke can include a thrombolytic therapy. The thrombolytic therapy can include administration of compounds selected from the group consisting of warfarin, aspirin, and thrombolytic drugs such as tissue plasminogen activators (e.g., alteplase, reteplase, tenecteplase), anistreplase, streptokinase, urokinase, and any other thrombolytic therapies known in the art.

The present treatment method can also comprise steps of altering treatments depending on the severity of the brain damage or the disease, condition, or event that caused the brain damage. For instance, in some embodiments the present methods include a step of characterizing the severity of an ischemic stroke depending on the concentration of the visinin-like protein that is present in the sample provided from the subject. Thereafter, the severity of the diagnosed ischemic stroke can also be used to direct and optimize treatment of the ischemic stroke.

Device

The presently-disclosed subject matter provides devices for detecting the presence of a visinin-like protein in a sample. In some embodiments the device is a lateral flow device (LFD). In some embodiments the lateral flow device can further comprise a vertical flow device. Exemplary devices can be stable at room temperature, and some devices can be stored for extended periods for future use.

In this respect, typically it can take up to 24 hours to quantify levels of the protein of interest using ELISAs. This relatively long time period is outside potentially therapeutic windows for many types of brain damage, including certain types of stroke and TBI. On the other hand, the present devices include lateral flow devices and vertical/lateral flow devices that allow for more rapid quantification of biomarkers (e.g., visinin-like protein) in subjects having or suspected of having TBI, stroke, or other brain damage. In general, lateral flow devices use material(s) that channel analytes (i.e., visinin-like proteins) into close proximity with target substances, such as antibodies, and can allow reaction and binding of the target substance to the analytes. Lateral movement of the sample in the lateral flow device allows for its controlled interaction with agents (e.g., antibodies) which can be located along the test channel(s), thereby allowing control of sequencing and timing of interactions.

The present lateral flow devices can employ passive means, such as capillary forces, of fluid movement that is not aided by a fluid pump. The present lateral flow devices can comprise natural or synthetic lateral flow materials. The materials can have porous structures that induce capillary forces. In some embodiments the lateral flow devices comprise capillary tubes or channels to direct flow. Exemplary materials for the devices include, but are not limited to, polysaccharides (e.g., cellulose materials such as paper and cellulose derivatives, such as cellulose acetate and nitrocellulose), polyether sulfone, polyethylene, nylon, polyvinylidene fluoride (PVDF), polyester, terephthalate (polyester) (PET), polymethylmethacrylate (PMMA), polystyrene, polypropylene, silica, inorganic materials, such as deactivated alumina, glass, diatomaceous earth, $MgSO_4$, ceramics, or other inorganic finely divided material uniformly dispersed in a porous polymer matrix, natural and/or synthetic cloth (e.g., cotton, nylon, or rayon), porous gels, such as silica gel, agarose, dextran, and gelatin, polymeric films, such as polyacrylamide; and the like.

The devices described herein can provide an efficient, accurate, and expedient manner in which to determine the presence of a visinin-like protein in a biological sample collected from a subject, and then potentially use this determination to make a diagnosis and/or prognosis within a clinically relevant time. In some embodiments the present devices can provide a diagnosis and/or prognosis within about 1 minute, 2 minutes, 3 minutes, 4 minutes, 5 minutes, 6 minutes, 7 minutes, 8 minutes, 9 minutes, 10 minutes, 15 minutes, 20 minutes, or 30 minutes of applying a sample to the device. In some embodiments the present devices can provide a diagnosis and/or prognosis in about 1 hour or less, about 2 hours or less, about 3 hours or less, about 4 hours or less, about 5 hours or less, or about 6 hours or less.

The present devices can be configured to detect a visinin-like protein in a sample at a minimum concentration or within a range of concentrations. The devices can thus detect the presence of a visinin-like protein so that the device can be utilized to diagnose and/or prognose a subject with brain damage or specific sources of brain damage such as TBI or a stroke. Some embodiments of the present devices can detect the presence of the visinin-like protein in a sample at a concentration of at least about 20 ng/ml or more. Some embodiments of the present devices can detect the presence of the visinin-like protein in a sample at a concentration of about 100 ng/ml, 200 ng/ml, 300 ng/ml, 400 ng/ml, 500 ng/ml, 600 ng/ml, 700 ng/ml, 800 ng/ml, 900 ng/ml, 1,000 ng/ml, 2,000 ng/ml, 3,000 ng/ml, 4,000 ng/ml, 5,000 ng/ml, 6,000 ng/ml, 7,000 ng/ml, 8,000 ng/ml, 9,000 ng/ml, 10,000 ng/ml, or more.

In some embodiments the device includes a sample portion, a conjugate portion, and a detection portion. Optionally, in some embodiments a wicking portion is provided downstream of the conjugate portion and is intended to collect any residual sample that flows through the device and past the detection portion. The sample portion, conjugate portion, detection portion, and wicking portion of embodied devices can be comprised of one continuous piece of a material or can be comprised of two or more distinct materials that may or may not be of the same type as one another. For example, the detection portion and the wicking portion can be formed from one continuous material, wherein the detection portion and wicking portion refer to different sections the piece of material, and in other embodiments the detection portion and the wicking portion can be comprised of two distinct materials.

The sample portion is provided to receive a sample. In some embodiments the sample portion can further receive a substance that permits the biological sample to cross through the device, such as a buffer solution (e.g., PBS). In some embodiments the biological samples comprise about 10 µL to about 1000 µl of a liquid sample.

Exemplary sample portions can further comprise an albumin eliminator for removing albumin from the biological sample, wherein "albumin eliminator" refers to any material, substance, or means for removing albumin from a substance. When the biological sample is whole blood or serum, embodiments of the sample portions can remove cells from the biological sample before it progresses to the other portions and membranes of the device. The cell and/or albumin removing means prevent the red blood cells or albumin from interfering with the test procedure and can help ensure that readings for the presence of a visinin-like protein are accurate. For example, red blood cells typically constitute about half of the volume of a blood sample. Unless the red blood cells are substantially removed, their presence can affect certain results that are sensitive to color. Hemoglobin can also interfere chemically with certain methods, and is removed by in some embodiments of the present methods and devices.

In some embodiments plasma is separated from red blood cells is by centrifugation prior to applying the sample to a device. Other exemplary methods for removing red blood cells are described in U.S. Pat. No. 4,477,575, which is incorporated herein by reference, and describes a blood filter made from glass fiber that can separate out red blood cells when whole blood is slowly trickled onto one side. Unsaturated aliphatic fatty acid or an ester thereof can also be provided in some devices, including on the sample portion of some devices, and can induce the formation of red blood cells that are distorted in shape and less flexible and malleable than normal red blood cells, making them less able to penetrate and flow through the device. The stiffer, less flexible cells cannot move easily and become trapped, while the liquid components of the sample can flow through the device and penetrate the detection portion for analysis. Those of ordinary skill will recognize other means and substances for removing red blood cells and other interfering substances from a sample that is intended for detecting a visinin-like protein.

The device further comprise a conjugate portion downstream of the sample portion that includes a conjugate. The conjugate can be disposed on a surface of the conjugate portion, impregnated into the conjugate portion, or the like. The conjugate includes a first antibody that is selective for the visinin-like protein that is bound (conjugated) to a detection probe. The first antibody and the detection probe can be bound by any means, including covalent bonds, electrostatic, bonds, other physical interactions, and the like.

The conjugate can be deposited along with one or more supporting substances. These supporting substances include, but are not limited to, poly (ethylene glycol) (PEG), sugars (i.e. dextran, maltodextrose), and surfactants, such as non-ionic surfactants (e.g., polysorbate 20 or 80, Triton X-100). Supporting substances can be added for a range of purposes, such as to reduce non-specific interactions between the sample and the device, obtain desired flow velocity, and to control the stability, viscosity, and release of the conjugate material.

The first antibody that comprises the conjugate can be of any class and be have dual or multiple antigen or epitope specificities. The first antibody can be a polyclonal antibody, particularly a humanized or an affinity-purified antibody from a human. The first antibody can be an antibody from an appropriate animal; e.g., a primate, goat, rabbit, mouse, or the like. If a paratope region is obtained from a non-human species, the target may be humanized to reduce immunogenicity of the non-human antibodies, for use in human diagnostic, prognostic, or therapeutic methods. Such a humanized antibody or fragment thereof can also be termed "chimeric." For example, a chimeric antibody includes non-human (e.g., murine) variable regions and human constant regions. Monoclonal antibodies are also suitable. A first antibody can include genetically engineered and/or recombinant proteins, whether single-chain or multiple-chain, which incorporate an antigen-binding site and otherwise function in vivo as immobilized target-binding moieties.

The first antibody can be selective for a visinin-like protein. In this manner, when a sample comprising a visinin-like protein is applied to a device, the conjugate will bind to the visinin-like protein via the first antibody, thereby labeling the visinin-like protein with the detection probe-labeled conjugate. The first antibody can be selective for one or more portions of the visinin-like protein, and in some embodiments is selective for the N-terminus, the C-terminus, or both of a visinin-like protein.

The detection probes are not particularly limited, and include substances that are detectable either visually or by an instrumental device. Exemplary detection probes can include, but are not limited to, fluorescent compounds (e.g., fluorescent, phosphorescent, etc.), radioactive compounds, visual labels (e.g., colored dye or metallic substance), liposomes or other vesicles containing signal-producing substances; enzymes and/or substrates, and combinations thereof. The detectable substance can be in the form of a particle, such as a nanobead. Exemplary particles include naturally occurring particles, such as nuclei, *mycoplasma*, plasmids, plastids, mammalian cells, unicellular microorganisms, polysaccharides, and the like. Exemplary particles can also be synthetic particles, such as particles comprised of polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and the like. Exemplary particles also include metallic substances, and in some embodiments the conjugate comprises nanogold beads conjugated to a first antibody that is selective for the visinin-like protein.

The present devices further include a detection portion disposed along the flow path that include one or more immobilized targeting substances selective for the conjugate and/or the visinin-like protein. In some embodiments the detection portion comprises a second antibody that is selective for the visinin-like protein, and in some instances the first antibody and the second antibody are selective for different portions of the visinin-like protein. Thus, samples that migrate from the sample portion can remain in the detecting portion if the samples include a visinin-like protein that binds to the immobilized second antibody. Likewise, if the visinin-like protein binds to a conjugate having the detection probe and the first antibody, then the resulting complex will remain in the detecting zone when the visinin-like protein binds to the second antibody.

The detection portion can also comprise a control zone that includes a third targeting substance (e.g., third antibody) that is selective for the first antibody. As discussed above, the first antibody is conjugated to a detection probe. Thus, if the conjugate does not bind to a visinin-like protein, it can pass across the second antibody and bind to the control zone. Detection of the conjugate that includes the first antibody and the detection probe on the control zone indicates that a sample flowed through the device but contained little to no visinin-like protein.

The targeting substances (e.g., second antibody and third antibody) can be immobilized in the detection zone as stripes. In this manner, a presence of the visinin-like protein can be detected if a complex including the conjugate and visinin-like protein bind to a location corresponding to the second antibody stripe. Similarly, a presence of the conjugate in a stripe corresponding to the control zone (e.g., third antibody) indicates the positive control line for the device.

An exemplary lateral flow device is shown in FIG. 1. The lateral flow device in FIG. 1 comprises a sample portion (E) that is upstream of a conjugate portion (D), which itself includes nanogold labeled first antibodies that can selectively bind a visinin-like protein. The nanogold labeled first antibody/antigen complex can then migrates along a detection portion (B) that is comprised of a separation membrane. The complex can be trapped by a second antibody against an alternate portion of the visinin-like protein as a thin stripe near the termination of the separation membrane. In addition to rapid reaction times between the visinin-like protein and the first antibody, the embodied lateral flow device offers the advantage of inclusion of additional membranes for cell separation and for removal of potentially interfering proteins (e.g, albumin).

EXAMPLES

The presently-disclosed subject matter is further illustrated by the following specific but non-limiting examples set forth below. The examples may include compilations of data that are representative of data gathered at various times during the course of development and experimentation related to the presently-disclosed subject matter.

Example 1

This Example describes a method for preparing a lateral flow device for detecting the presence of VILIP-1 in a biological sample. As shown in FIG. 1, the lateral flow device comprises of a combination of membranes that remove cells (e.g., whole blood) and serum albumin (e.g., rat or human) from a biological sample, nanogold labeled anti VILIP-1 raised against the N terminus of human VILIP-1, and a narrow line near the terminal end of anti-VILIP-1 antibody raised against the C terminus of human VILIP-1. More specifically, and still referring to FIG. 1, the lateral flow device comprised a laminate backing (A; MIBA-010; Diagnostic Consulting Network, Carlsbad, Calif.), a sample portion for receiving a biological sample (E; Vivid Plasma Separation-GX; Pall Corporation, Port Washington, N.Y.), a conjugate portion (D; Pall, Grade 896), a detection portion (B; Unisart CN140 Nitrocellulose Membrane, 42 mm; Sartorius Stedin North America Inc, Bohemia, N.Y.), and a wicking portion (C; Whatman 470; GE Healthcare Life Sciences, Piscataway, N.J.).

To prepare the antibodies, all antibodies were dialyzed against water overnight at 4° C., lyophilized, and re-suspended in 1× PBS (pH 7.4) at concentrations described in this Example. Next, monoclonal VILIP-1 PL-A2 (Abnova, Taipei City, Neihu District, Taiwan) at a concentration of 2 mg/mL was conjugated to 40 nm gol sol per manufacturers' instructions (BioAssay Works, Fredrick, Md., USA) with modification. Briefly 6 µg of VILIP-1 PL-A2 was conjugated with 0.5 mL of 40 nm Naked Gold Sol (OD 7.5) for 5 min at room temperature with constant gentle agitation. Conjugation was stopped by the addition of 10% BSA solution for 1 hr at room temperature with constant agitation followed by the treatment with N-ethylmalemide at a final concentration of 20 nM for 1 hr at room temperature with constant agitation.

The antibody-nanogold conjugate was then added to the conjugate portion. Specifically, the mouse anti-VILIP-1 PL-A2/nanogold conjugate was mixed with 25% sucrose/ 1% Tween 20 in PBS and Rabbit anti-goat IgG Dressed Gold (BioAssay Works) in a 1:0.6:1.7 ratio and applied to 25% sucrose/1% Tween 20 in PBS pre-coated at 10 uL/cm Pall Grade 8964 conjugate portion (Pall, Port Washington, N.Y., USA) using an Air-Jet sprayer (BioDot, Irvine, Calif., USA) at a volume of 70 uL/cm and dried for 1 hr at 37° C. Conjugate portions were stored in sealed sample bags with desiccant at room temperature.

Next, the Unistart CN140 cellulase nitrate membranes (detection portion) were applied to the MIBA-010 laminate backing Rabbit anti-VILIP-1 K-25 (Santa Cruz Biotechnology, Santa Cruz, Calif.) at a final concentration of 0.5 mg/mL and Goat Serum (Invitrogen, Carlsbad, Calif.,) were applied in parallel stripes using Bio-Jet equipment (BioDot) at 4 ug/cm and 16 uL/cm and 30 and 37 mm from the bottom of the lateral flow device, respectively. The membranes were dried for 1 hr at 37° C. blocked in 1% dry milk/PBS for 15 minutes, washed 3 times in PBS, and dried for 1 hr at 37° C. Backed cellulose nitrate membranes were stored in sealed sample bags with desiccant at room temperature.

Sheep anti-rat (Bethyl Laboratories, Montgomery, Tex., USA; 4 mg/mL) or anti-human albumin (Santa Cruz) was then applied to the Vivid Plasma Separation-GX (Pall Corporation) sample portions using a Bio-Jet sprayer (BioDot) at 60 ug/cm and dried for 1 hr at 37° C. Albumin eliminator/ sample portions were stored in sealed bags with desiccant at room temperature.

The stored and/or treated membranes were then assembled into the lateral flow device. First, a 16 mm wide Whatman 470 wicking portion (GE Healthcare Life Sciences) was overlaid at the top of the cellulose nitrate membrane (detection portion) parallel to the test and control lines and was attached to the laminate backing. A 13 mm conjugate portion was overlaid at the bottom of the cellulose nitrate parallel to the test and control lines and was attached to laminate backing 2 mm from the bottom of the test strip. A 15 mm sample portion was adhered to the bottom of the test strip overlaying the conjugate portion. The Assembled membranes were cut into 4 mm wide strips and fitted into MICA-010 2-hole cassettes (Diagnostic Consulting Network, Carlsbad, Calif.) assemblies. Assembled lateral flow devices were stored in sealed sample bags with desiccant at room temperature for future use.

Example 2

This Example describes procedures conducted to evaluate how the embodiments of lateral flow devices that were prepared in Example 1 can be used to detect the presence of VILIP-1 in subjects having brain damage, including brain damage caused by ischemic stroke or TBI.

Figure 2:
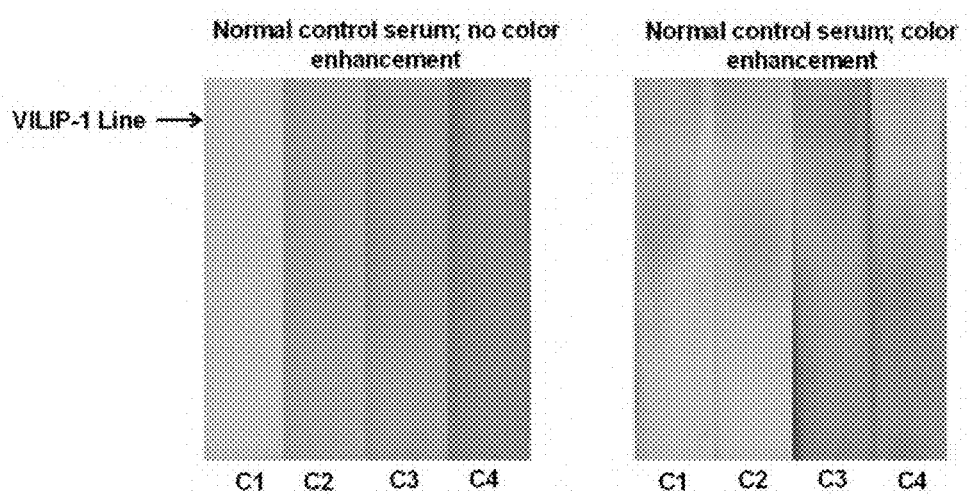
FIG. 2 includes images showing VILIP-1 levels in normal control serum measured using a lateral flow device.

First, using recombinant VILIP-1 as a standard protein, a limit of detection of 0.2 ng/ml serum and a linear response between 0.2 ng/ml and 7.0 ng/ml was detected ($r^2$=0.91). FIG. 2 shows levels of VILIP-1 in normal control serum are below the limit of detection. Thus, the lateral flow devices were capable of detecting the presence of VILIP-1 in biological samples.

To determine if serum VILIP-1 levels change in due to ischemic stroke, animals were subjected to a 1 hour middle cerebral artery occlusion (MCAO) using the *Zea Longa* method. Specifically, nine three-month-old Sprague-Dawley rats (250-300 g) were subjected to a 1 hour ischemic event induced by suture occlusion of the middle cerebra artery. Control animals (N=5) were subjected to surgical preparation but without occlusion. Blood samples (50 µL) were obtained from the left femoral artery prior to occlusion, when the occlude was removed (pre-reperfusion), 15 minutes after initiation of reperfusion, and 24 hour post reperfusion.

To examine serum levels of VILIP-1 in TBI, four 3 month old Sprague-Dawley rats were subjected to mild or moderate controlled cortical impact (CCI) or sham surgery in which a portion of the skull was removed but without brain impact. Control rats consisted of surgery naïve rates (N=4) anesthetized but without any surgical manipulation. For analyses, whole blood (100-200 µL) samples were taken prior to beginning surgeries and 1, 2, and 3 hour post injury from tail nicks of the young adult male Sprague-Dawley rats under isoflurane anesthesia (2%).

Immediately following collection, whole blood (10 µL) or serum (10 µL) samples were applied to the asymmetric sample portion, resulting in the removal of red blood cells from the sample. Three minutes post sample loading 20 µL of lateral flow device sample buffer (0.5% Surfactant 10G, 0.8 USP heparin/mL) was applied directly to the conjugate portion to prevent lysis of red blood cells trapped in the asymmetrical sample portion and facilitate migration of the sample through the cellulose nitrate membrane. The test and control lines were observed for color development at 15 minutes post-sample loading, and images were captured for analysis. Gold Enhance LM/Blot (Nanoprobes, Yaphank, N.Y., USA) was prepared per manufacturer's directions and 20 μL was applied directly to the lateral flow device membranes. Color development was observed 15 minutes post-color enhancement and images were taken for analysis. The remaining whole blood samples were centrifuged at 15,000×g for 5 minutes and the serum samples were collected and stored at −80° C. for later analysis.

Example 3

This Example describes the relationship between VILIP-1 levels and brain damage that were observed using the procedures described in Example 2. Specifically, this Example describes how VILIP-1 levels were affected by the induced ischemic stroke and TBI in rat subjects.

Figure 3:
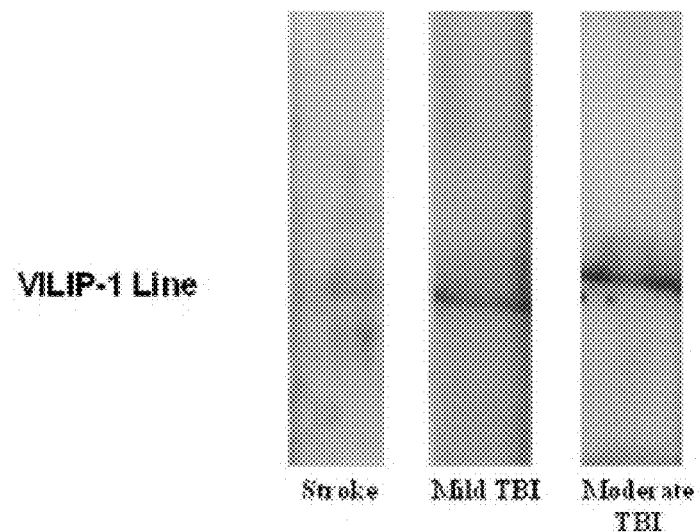
FIG. 3 includes images showing VILIP-1 levels for ischemic stroke, mild traumatic brain injury (TBI), and moderate TBI samples from animal subjects.

As described above, whole blood (10 μL) were analyzed at the time of draw and the remaining blood samples were centrifuged to prepare serum which was analyzed from all time points later. FIG. 3 shows that levels of VILIP-1 in serum were considerably higher in mild TBI compared to ischemic stroke 1 hour and 15 minutes post injury, thereby suggesting that TBI can induce more pronounced neuronal injury (i.e., brain damage). Without being bound by theory or mechanism, VILIP-1 levels for subjects having experienced hemorrhagic stroke can be comparable to those observed in TBI because hemorrhagic stroke can cause severe tissue damage. Thus, optionally when combined with clinical presentation, the presence of VILIP-1, including at concentrations below a level corresponding to TBI or hemorrhagic stroke, can provide a delineation of ischemic stroke from hemorrhagic stroke.

Figure 4:
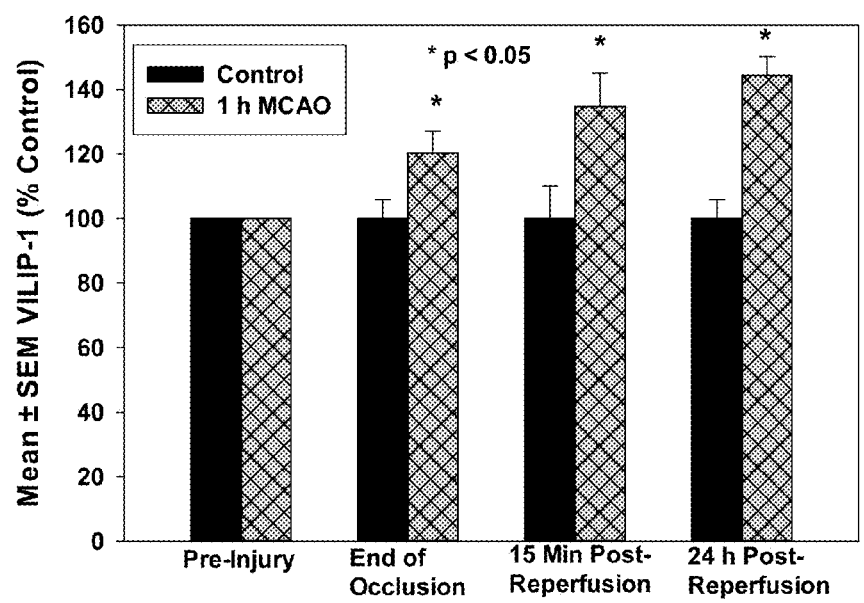
FIG. 4 includes a plot showing mean±standard error of the mean (SEM) VILIP-1 levels in rats subjected to an ischemic event induced by suture occlusion of the middle cerebral artery pre-injury, at the end of the 1 hour of occlusion, 15 minutes after the initiation of reperfusion, and 24 hours post reperfusion.
Figure 5:
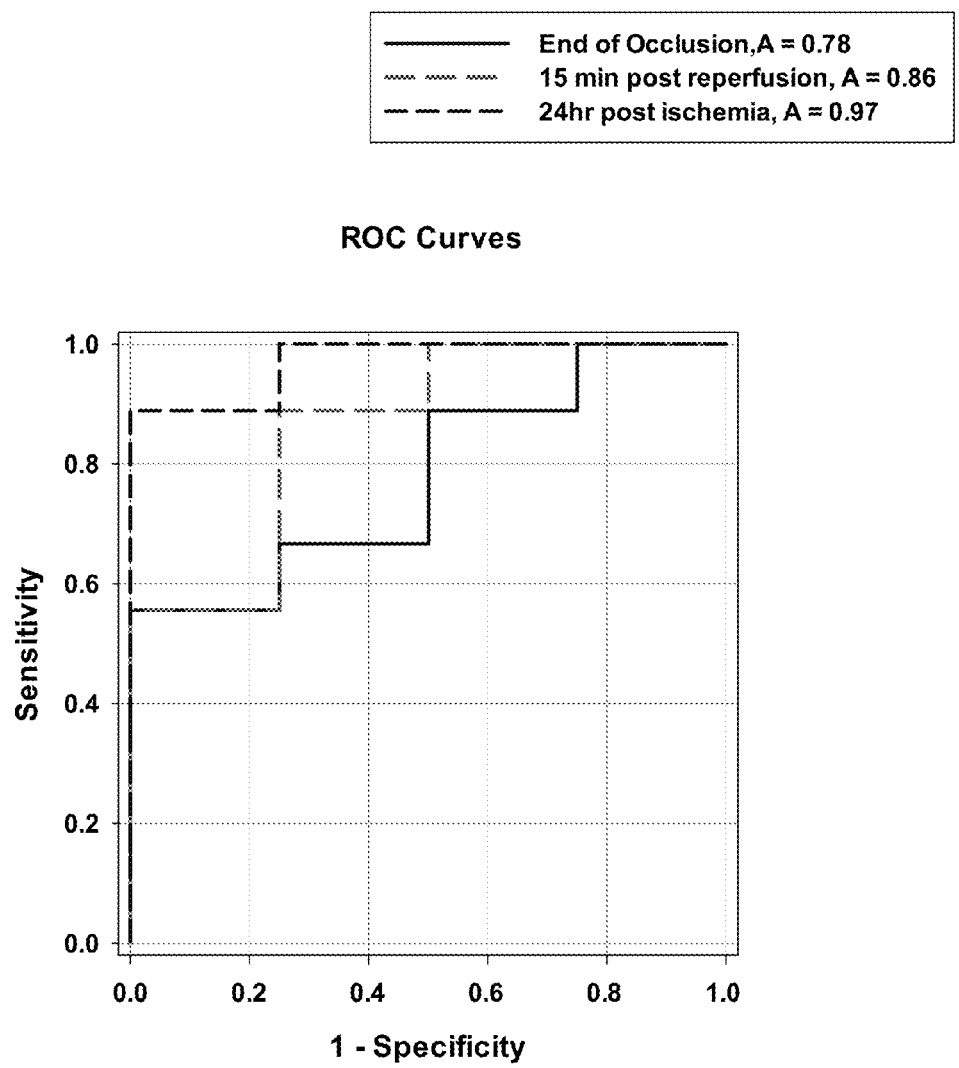
FIG. 5 includes a plot showing receiver operating characteristic (ROC) curves for VILIP-1 levels in serum samples from rats subjected to middle cerebral artery occlusion as a model of ischemic stroke.

With regard to the rats having the induced ischemic stroke, FIG. 4 shows serum levels of VILIP-1 increased significantly immediately after the occlude was removed. FIG. 4 also suggests that serum levels of VILIP-1 reached a maximum after initiation of reperfusion, and remained elevated 24 hours post injury. Correlation analyses showed VILIP-1 levels were significantly correlated (r=0.61) with lesion volume measured 24 hour post-injury. FIG. 5 shows receiver operating characteristic (ROC) curves for VILIP-1 levels at each time point and shows sensitivity/specificity values of 89 and 75% with an area under the curve (AUC) of 86% for 15 minutes post reperfusion and 100% sensitivity/75% specificity and an AUC=97% for 24 hours post reperfusion.

Figure 6:
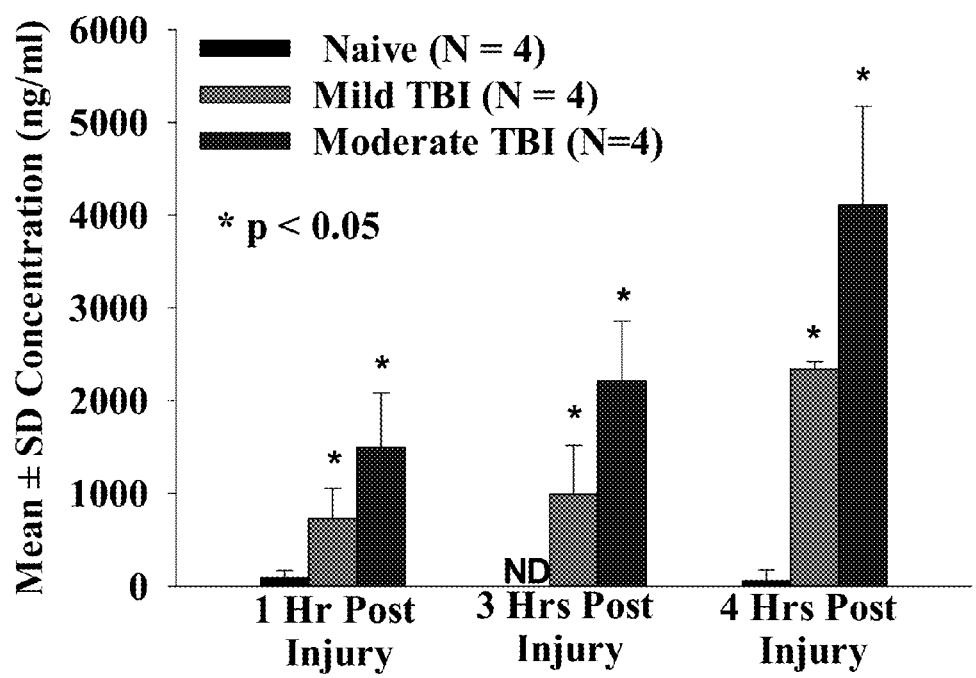
FIG. 6 shows mean±SEM VILIP-1 levels in serum from surgery naïve rats or rats subjected to mild or moderate TBI that were taken 1, 3, and 4 hours post injury.
Figure 7:
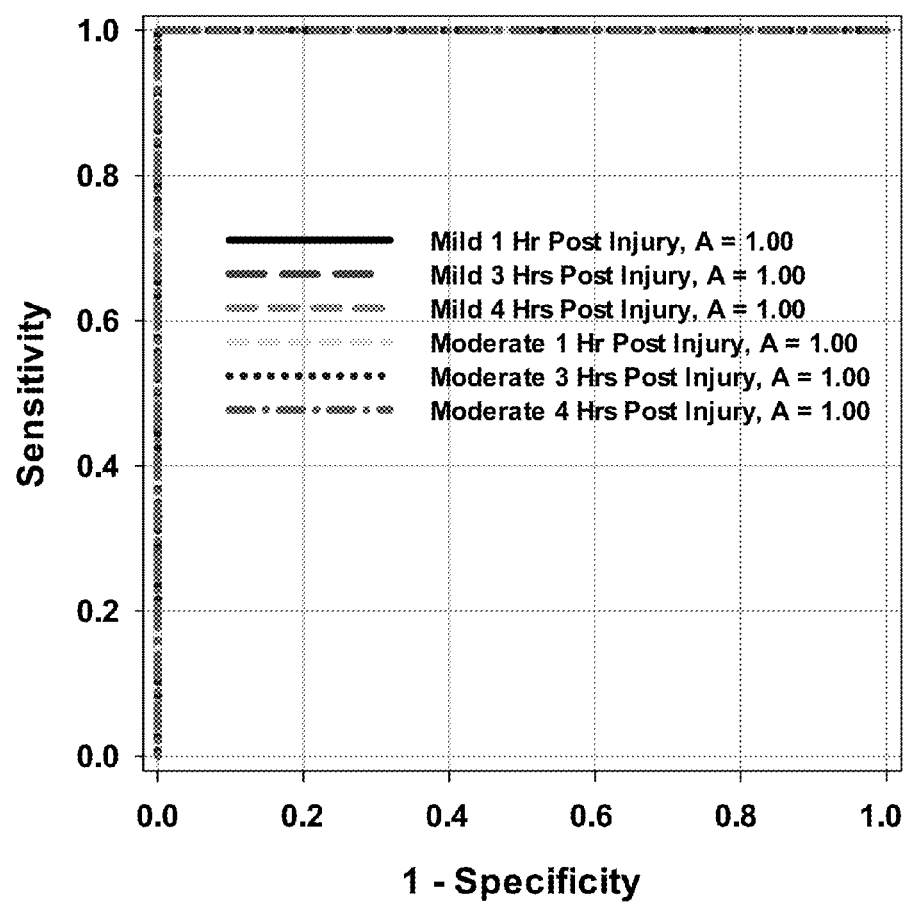
FIG. 7 includes a chart showing receiver operating characteristic (ROC) curves for VILIP-1 levels in serum samples from rats that were taken 1, 3, and 4 hours following mild or moderate TBI.

For the rats subjected to TBI, FIG. 6 shows mean±SEM serum VILIP-1 levels, and shows that VILIP-1 levels in serum progressively increased 1 hour, 3 hours, and 4 hours post injury for both mild TBI and moderate TBI test groups. FIG. 7 shows ROC for VILIP-1 in the subjects having mold TBI and moderate TBI.

Example 4

This Example describes a diagnostic procedure conducted on human samples using the methods and device described in Examples 1 and 2.

Figure 8:
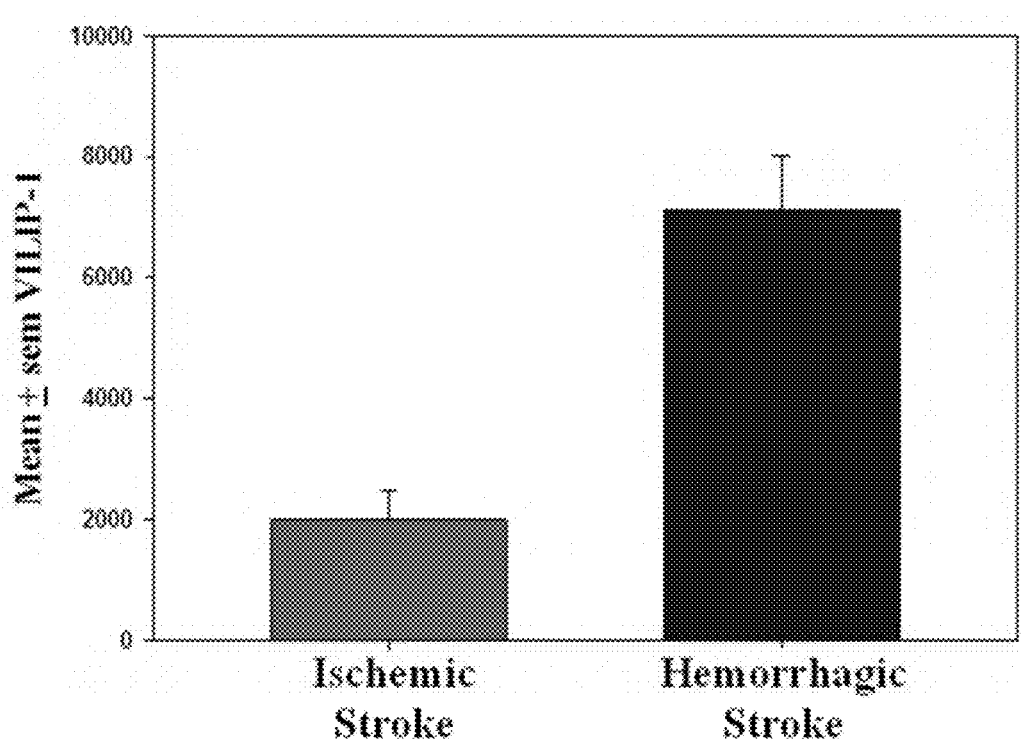
FIG. 8 includes a chart showing VILIP-1 levels in serum from two subjects with hemorrhagic stroke and two subjects with ischemic stroke.
Figure 9:
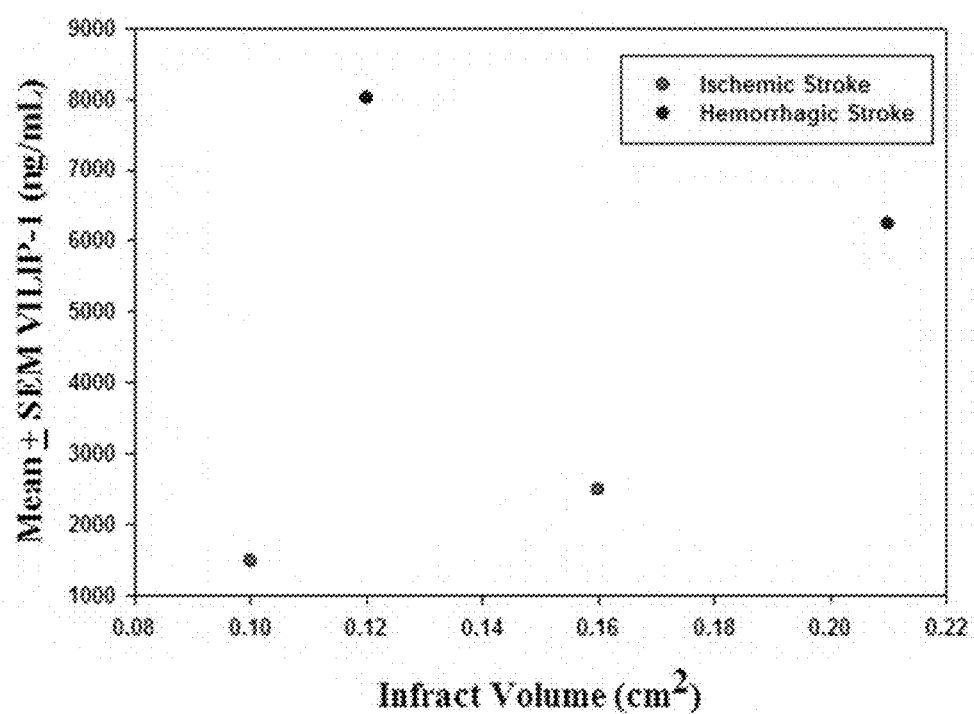
FIG. 9 includes a chart showing VILIP-1 levels relative to infarct volume for two subjects with hemorrhagic stroke and two subjects with ischemic stroke.

Serum samples from a commercial source that were taken from patients 6 hours after ischemic (N=2) or hemorrhagic (N=2) stroke. Serum samples (10 μl) were applied to LFDs as described above, and intensity of the trapped nanogold was quantified using Scion Image Analysis. Quantification of VILIP-1 levels was carried out using a calibration curve constructed using increasing concentrations of standard VILIP-1 prepared in 70% control serum. FIG. 8 shows results of the analysis of serum samples from two subjects with hemorrhagic stroke and two subjects with ischemic stroke and showed mean±SD concentrations of 1988.7±714.4 ng/ml for the ischemic stroke patients and 7125.8±1254.1 ng/ml for subjects with hemorrhagic stroke. The measured values were positively related to infarct volume measured by MRI (FIG. 9).

It will be understood that various details of the presently disclosed subject matter can be changed without departing from the scope of the subject matter disclosed herein. Furthermore, the description provided herein is for the purpose of illustration only, and not for the purpose of limitation.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are described herein.

The terms "comprising", "including," and "having" are intended to be inclusive and mean that there may be additional elements other than the listed elements.

Following long-standing patent law convention, the terms "a", "an", and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. Such references include, but are not limited to, publications, patents, and patent applications. All such references are incorporated herein by reference, including the references set forth in the following list:

REFERENCES

1. Faul, M., et al., *Traumatic brain injury in the United States: emergency department visits, hospitalizations, and deaths.*, 2010.

2. Coronado, V. G., et al., *Surveillance for traumatic brain injury-related deaths—United States, 1997-2007.* MMWR Surveill Summ, 2011. 60(5): p. 1-32.
3. Farkas, O., et al., *Spectrin breakdown products in the cerebrospinal fluid in severe head injury-preliminary observations.* Acta Neurochir (Wien), 2005. 147(8): p. 855-61.
4. Haskins, W. E., et al., *Rapid discovery of putative protein biomarkers of traumatic brain injury by SDS-PAGE-capillary liquid chromatography-tandem mass spectrometry.* J Neurotrauma, 2005. 22(6): p. 629-44.
5. Pineda, J. A., K. K. Wang, and R. L. Hayes, *Biomarkers of proteolytic damage following traumatic brain injury.* Brain Pathol, 2004. 14(2): p. 202-9.
6. Smith, D. H., et al., *Protein accumulation in traumatic brain injury.* Neuromolecular Med, 2003. 4(1-2): p. 59-72.
7. Ommaya, A. K., et al., *Causation, incidence, and costs of traumatic brain injury in the U.S. military medical system.* J Trauma, 1996. 40(2): p. 211-7.
8. Taylor, B. C., et al., *Prevalence and costs of co-occurring traumatic brain injury with and without psychiatric disturbance and pain among Afghanistan and Iraq War Veteran V.A. users.* Med Care, 2012. 50(4): p. 342-6.
9. Agoston, D. V. and M. Elsayed, *Serum-based protein biomarkers in blast-induced traumatic brain injury spectrum disorder.* Front Neurol, 2012. 3: p. 107.
10. Minino, A. M., et al., *Deaths: final data for 2008.* Natl Vital Stat Rep, 2011. 59(10): p. 1-126.
11. Roger, V. L., et al., *Heart disease and stroke statistics—2012 update: a report from the American Heart Association.* Circulation, 2012. 125(1): p. e2-e220.
12. Sharma, R. and D. T. Laskowitz, *Biomarkers in traumatic brain injury.* Current neurology and neuroscience reports, 2012. 12(5): p. 560-9.
13. Shenton, M. E., et al., *A review of magnetic resonance imaging and diffusion tensor imaging findings in mild traumatic brain injury.* Brain Imaging Behav, 2012. 6(2): p. 137-92.
14. Garnett, M. R., et al., *Early proton magnetic resonance spectroscopy in normal-appearing brain correlates with outcome in patients following traumatic brain injury.* Brain, 2000. 123 (Pt 10): p. 2046-54.
15. Al-Samsam, R. H., B. Alessandri, and R. Bullock, *Extracellular N-acetyl-aspartate as a biochemical marker of the severity of neuronal damage following experimental acute traumatic brain injury.* J Neurotrauma, 2000. 17(1): p. 31-9.
16. Elder, G. A., et al., *Blast-induced mild traumatic brain injury.* Psychiatr Clin North Am, 2010. 33(4): p. 757-81.
17. Hergenroeder, G. W., et al., *Biomarkers in the clinical diagnosis and management of traumatic brain injury.* Mol Diagn Ther, 2008. 12(6): p. 345-58.
18. Levin, H. S., et al., *Diffusion tensor imaging of mild to moderate blast-related traumatic brain injury and its sequelae.* J Neurotrauma, 2010. 27(4): p. 683-94.
19. Rosenfeld, J. V. and N. L. Ford, *Bomb blast, mild traumatic brain injury and psychiatric morbidity: a review.* Injury, 2010. 41(5): p. 437-43.
20. Trudeau, D. L., et al., *Findings of mild traumatic brain injury in combat veterans with PTSD and a history of blast concussion.* J Neuropsychiatry Clin Neurosci, 1998. 10(3): p. 308-13.
21. Drake, A. I., et al., *Routine TBI screening following combat deployments.* NeuroRehabilitation, 2010. 26(3): p. 183-9.
22. Thompson, J. M., K. C. Scott, and L. Dubinsky, *Battlefield brain: unexplained symptoms and blast-related mild traumatic brain injury.* Can Fam Physician, 2008. 54(11): p. 1549-51.
23. Wolf, S. J., et al., *Blast injuries.* Lancet, 2009. 374 (9687): p. 405-15.
24. Zetterberg, H., D. H. Smith, and K. Blennow, *Biomarkers of mild traumatic brain injury in cerebrospinal fluid and blood.* Nature reviews. Neurology, 2013. 9(4): p. 201-10.
25. Baugh, C. M., et al., *Chronic traumatic encephalopathy: neurodegeneration following repetitive concussive and subconcussive brain trauma.* Brain imaging and behavior, 2012. 6(2): p. 244-54.
26. Adams, H. P., Jr., et al., *Guidelines for the early management of adults with ischemic stroke: a guideline from the American Heart Association/American Stroke Association Stroke Council, Clinical Cardiology Council, Cardiovascular Radiology and Intervention Council, and the Atherosclerotic Peripheral Vascular Disease and Quality of Care Outcomes in Research Interdisciplinary Working Groups: the American Academy of Neurology affirms the value of this guideline as an educational tool for neurologists.* Stroke, 2007. 38(5): p. 1655-711.
27. Whiteley, W., et al., *Blood markers for the prognosis of ischemic stroke: a systematic review.* Stroke; a journal of cerebral circulation, 2009. 40(5): p. e380-9.
28. *Tissue plasminogen activator for acute ischemic stroke. The National Institute of Neurological Disorders and Stroke rt-PA Stroke Study Group.* N Engl J Med, 1995. 333(24): p. 1581-7.
29. Barber, P. A., et al., *Why are stroke patients excluded from TPA therapy? An analysis of patient eligibility.* Neurology, 2001. 56(8): p. 1015-20.
30. Johnson, V. E., W. Stewart, and D. H. Smith, *Axonal pathology in traumatic brain injury.* Experimental neurology, 2013. 246: p. 35-43.
31. Wolf, J. A., et al., *Traumatic axonal injury induces calcium influx modulated by tetrodotoxin-sensitive sodium channels.* The Journal of neuroscience: the official journal of the Society for Neuroscience, 2001. 21(6): p. 1923-30.
32. Saatman, K. E., J. Creed, and R. Raghupathi, *Calpain as a therapeutic target in traumatic brain injury.* Neurotherapeutics: the journal of the American Society for Experimental NeuroTherapeutics, 2010. 7(1): p. 31-42.
33. Barkhoudarian, G., D. A. Hovda, and C. C. Giza, *The molecular pathophysiology of concussive brain injury.* Clinics in sports medicine, 2011. 30(1): p. 33-48, vii-iii.
34. Giza, C. C. and D. A. Hovda, *The Neurometabolic Cascade of Concussion.* Journal of athletic training, 2001. 36(3): p. 228-235.
35. Donkin, J. J. and R. Vink, *Mechanisms of cerebral edema in traumatic brain injury: therapeutic developments.* Curr Opin Neurol, 2010. 23(3): p. 293-9.
36. Ghirnikar, R. S., Y. L. Lee, and L. F. Eng, *Inflammation in traumatic brain injury: role of cytokines and chemokines.* Neurochem Res, 1998. 23(3): p. 329-40.
37. Lenzlinger, P. M., et al., *The duality of the inflammatory response to traumatic brain injury.* Mol Neurobiol, 2001. 24(1-3): p. 169-81.
38. Morganti-Kossmann, M. C., et al., *Inflammatory response in acute traumatic brain injury: a double-edged sword.* Curr Opin Crit Care, 2002. 8(2): p. 101-5.
39. Nortje, J. and D. K. Menon, *Traumatic brain injury: physiology, mechanisms, and outcome.* Curr Opin Neurol, 2004. 17(6): p. 711-8.

40. Vink, R., A. J. Nimmo, and I. Cernak, *An overview of new and novel pharmacotherapies for use in traumatic brain injury.* Clin Exp Pharmacol Physiol, 2001. 28(11): p. 919-21.
41. Eddleston, M. and L. Mucke, *Molecular profile of reactive astrocytes—implications for their role in neurologic disease.* Neuroscience, 1993. 54(1): p. 15-36.
42. Sawada, M., et al., *Production of tumor necrosis factor-alpha by microglia and astrocytes in culture.* Brain Res, 1989. 491(2): p. 394-7.
43. Rosenberg, G. A., et al., *Tumor necrosis factor-alpha-induced gelatinase B causes delayed opening of the blood-brain barrier: an expanded therapeutic window.* Brain Res, 1995. 703(1-2): p. 151-5.
44. Csuka, E., et al., *IL-10 levels in cerebrospinal fluid and serum of patients with severe traumatic brain injury: relationship to IL-6, TNF-alpha, TGF-beta1 and blood-brain barrier function.* J Neuroimmunol, 1999. 101(2): p. 211-21.
45. Goodman, J. C., et al., *Elevation of tumor necrosis factor in head injury.* J Neuroimmunol, 1990. 30(2-3): p. 213-7.
46. Ross, S. A., et al., *The presence of tumour necrosis factor in CSF and plasma after severe head injury.* Br J Neurosurg, 1994. 8(4): p. 419-25.
47. Helmy, A., et al., *The cytokine response to human traumatic brain injury: temporal profiles and evidence for cerebral parenchymal production.* J Cereb Blood Flow Metab, 2011. 31(2): p. 658-70.
48. Shiozaki, T., et al., *Cerebrospinal fluid concentrations of anti-inflammatory mediators in early-phase severe traumatic brain injury.* Shock, 2005. 23(5): p. 406-10.
49. Hillman, J., et al., *A microdialysis technique for routine measurement of macromolecules in the injured human brain.* Neurosurgery, 2005. 56(6): p. 1264-8; discussion 1268-70.
50. Hillman, J., et al., *Variations in the response of interleukins in neurosurgical intensive care patients monitored using intracerebral microdialysis.* J Neurosurg, 2007. 106(5): p. 820-5.
51. Morganti-Kossmann, M. C., et al., *TGF-beta is elevated in the CSF of patients with severe traumatic brain injuries and parallels blood-brain barrier function.* J Neurotrauma, 1999. 16(7): p. 617-28.
52. Povlishock, J. T., *The classification of traumatic brain injury (TBI) for targeted therapies.* J Neurotrauma, 2008. 25(7): p. 717-8.
53. Ravizza, T., et al., *Dynamic induction of the long pentraxin PTX3 in the CNS after limbic seizures: evidence for a protective role in seizure-induced neurodegeneration.* Neuroscience, 2001. 105(1): p. 43-53.
54. Frugier, T., et al., *In situ detection of inflammatory mediators in post mortem human brain tissue after traumatic injury.* J Neurotrauma, 2010. 27(3): p. 497-507.
55. Kossmann, T., et al., *Interleukin-8 released into the cerebrospinal fluid after brain injury is associated with blood-brain barrier dysfunction and nerve growth factor production.* J Cereb Blood Flow Metab, 1997. 17(3): p. 280-9.
56. Lumpkins, K., et al., *Plasma levels of the beta chemokine regulated upon activation, normal T cell expressed, and secreted (RANTES) correlate with severe brain injury.* J Trauma, 2008. 64(2): p. 358-61.
57. Heizmann, C. W., G. Fritz, and B. W. Schafer, *S100 proteins: structure, functions and pathology.* Front Biosci, 2002. 7: p. d1356-68.
58. Goncalves, C. A., M. C. Leite, and M. C. Guerra, *Adipocytes as an Important Source of Serum S100B and Possible Roles of This Protein in Adipose Tissue.* Cardiovasc Psychiatry Neurol, 2010. 2010: p. 790431.
59. Pang, X., et al., *S100B protein as a possible participant in the brain metastasis of NSCLC.* Med Oncol, 2012. 29(4): p. 2626-32.
60. Sorci, G., et al., *The many faces of S100B protein: when an extracellular factor inactivates its own receptor and activates another one.* Ital J Anat Embryol, 2010. 115(1-2): p. 147-51.
61. Raabe, A., C. Grolms, and V. Seifert, *Serum markers of brain damage and outcome prediction in patients after severe head injury.* British journal of neurosurgery, 1999. 13(1): p. 56-9.
62. Raabe, A., et al., *Jugular venous and arterial concentrations of serum S-100B protein in patients with severe head injury: a pilot study.* Journal of neurology, neurosurgery, and psychiatry, 1998. 65(6): p. 930-2.
63. Woertgen, C., et al., *Comparison of clinical, radiologic, and serum marker as prognostic factors after severe head injury.* The Journal of trauma, 1999. 47(6): p. 1126-30.
64. Egea-Guerrero, J. J., et al., *Accuracy of the S100beta protein as a marker of brain damage in traumatic brain injury.* Brain Inj, 2012. 26(1): p. 76-82.
65. Unden, J., et al., *Serum S100B levels in patients with cerebral and extracerebral infectious disease.* Scand J Infect Dis, 2004. 36(1): p. 10-3.
66. Savola, O., et al., *Effects of head and extracranial injuries on serum protein S100B levels in trauma patients.* J Trauma, 2004. 56(6): p. 1229-34; discussion 1234.
67. Torabian, S. and M. Kashani-Sabet, *Biomarkers for melanoma.* Curr Opin Oncol, 2005. 17(2): p. 167-71.
68. Foerch, C., et al., *Diagnostic accuracy of plasma glial fibrillary acidic protein for differentiating intracerebral hemorrhage and cerebral ischemia in patients with symptoms of acute stroke.* Clin Chem, 2012. 58(1): p. 237-45.
69. Metting, Z., et al., *GFAP and S100B in the acute phase of mild traumatic brain injury.* Neurology, 2012. 78(18): p. 1428-33.
70. Vos, P. E., et al., *GFAP and S100B are biomarkers of traumatic brain injury: an observational cohort study.* Neurology, 2010. 75(20): p. 1786-93.
71. Marangos, P. J. and D. E. Schmechel, *Neuron specific enolase, a clinically useful marker for neurons and neuroendocrine cells.* Annu Rev Neurosci, 1987. 10: p. 269-95.
72. Thomas, D. G., J. W. Palfreyman, and J. G. Ratcliffe, *Serum-myelin-basic-protein assay in diagnosis and prognosis of patients with head injury.* Lancet, 1978. 1(8056): p. 113-5.
73. Ross, S. A., et al., *Neuron-specific enolase as an aid to outcome prediction in head injury.* Br J Neurosurg, 1996. 10(5): p. 471-6.
74. Yamazaki, Y., et al., *Diagnostic significance of serum neuron-specific enolase and myelin basic protein assay in patients with acute head injury.* Surg Neurol, 1995. 43(3): p. 267-70; discussion 270-1.
75. Papa, L., et al., *Ubiquitin C-terminal hydrolase is a novel biomarker in humans for severe traumatic brain injury.* Crit Care Med, 2010. 38(1): p. 138-44.
76. Brophy, G. M., et al., *Biokinetic analysis of ubiquitin C-terminal hydrolase-L1 (UCH-L1) in severe traumatic brain injury patient biofluids.* J Neurotrauma, 2011. 28(6): p. 861-70.
77. Cardali, S. and R. Maugeri, *Detection of alphaII-spectrin and breakdown products in humans after severe traumatic brain injury.* J Neurosurg Sci, 2006. 50(2): p. 25-31.

78. Foerch, C., et al., *Invited article: searching for oracles? Blood biomarkers in acute stroke*. Neurology, 2009. 73(5): p. 393-9.
79. Jensen, M. B., et al., *Potential biomarkers for the diagnosis of stroke*. Expert review of cardiovascular therapy, 2009. 7(4): p. 389-93.
80. Jickling, G. C. and F. R. Sharp, *Blood biomarkers of ischemic stroke*. Neurotherapeutics, 2011. 8(3): p. 349-60.
81. Herrmann, M., et al., *Release of glial tissue-specific proteins after acute stroke: A comparative analysis of serum concentrations of protein S-100B and glial fibrillary acidic protein*. Stroke; a journal of cerebral circulation, 2000. 31(11): p. 2670-7.
82. Wunderlich, M. T., et al., *Early neurobehavioral outcome after stroke is related to release of neurobiochemical markers of brain damage*. Stroke; a journal of cerebral circulation, 1999. 30(6): p. 1190-5.
83. Wunderlich, M. T., C. W. Wallesch, and M. Goertler, *Release of neurobiochemical markers of brain damage is related to the neurovascular status on admission and the site of arterial occlusion in acute ischemic stroke*. Journal of the neurological sciences, 2004. 227(1): p. 49-53.
84. Ilg, E. C., B. W. Schafer, and C. W. Heizmann, *Expression pattern of S100 calcium-binding proteins in human tumors*. International journal of cancer. Journal international du cancer, 1996. 68(3): p. 325-32.
85. Lamers, K. J., et al., *Protein S-100B, neuron-specific enolase (NSE), myelin basic protein (MBP) and glial fibrillary acidic protein (GFAP) in cerebrospinal fluid (CSF) and blood of neurological patients*. Brain research bulletin, 2003. 61(3): p. 261-4.
86. Steiner, J., et al., *S100B is expressed in, and released from, OLN-93 oligodendrocytes: Influence of serum and glucose deprivation*. Neuroscience, 2008. 154(2): p. 496-503.
87. Zimmer, D. B., et al., *The S100 protein family: history, function, and expression*. Brain research bulletin, 1995. 37(4): p. 417-29.
88. Lynch, J. R., et al., *Novel diagnostic test for acute stroke*. Stroke; a journal of cerebral circulation, 2004. 35(1): p. 57-63.
89. Reynolds, M. A., et al., *Early biomarkers of stroke*. Clinical chemistry, 2003. 49(10): p. 1733-9.
90. Laskowitz, D. T., et al., *Clinical usefulness of a biomarker-based diagnostic test for acute stroke: the Biomarker Rapid Assessment in Ischemic Injury (BRAIN) study*. Stroke; a journal of cerebral circulation, 2009. 40(1): p. 77-85.
91. Ikura, M., *Calcium binding and conformational response in EF-hand proteins*. Trends in biochemical sciences, 1996. 21(1): p. 14-7.
92. Stejskal, D., et al., *Determination of serum visinin like protein-1 and its potential for the diagnosis of brain injury due to the stroke: a pilot study*. Biomedical papers of the Medical Faculty of the University Palacky, Olomouc, Czechoslovakia, 2011. 155(3): p. 263-8.
93. Baumann, B., et al., *Reduced volume of limbic system-affiliated basal ganglia in mood disorders: preliminary data from a postmortem study*. J Neuropsychiatry Clin Neurosci, 1999. 11(1): p. 71-8.
94. An, W. F., et al., *Modulation of A-type potassium channels by a family of calcium sensors*. Nature, 2000. 403(6769): p. 553-6.
95. Weiss, J. L., D. A. Archer, and R. D. Burgoyne, *Neuronal Ca2+ sensor-1/frequenin functions in an autocrine pathway regulating Ca2+ channels in bovine adrenal chromaffin cells*. The Journal of biological chemistry, 2000. 275(51): p. 40082-7.
96. Carrion, A. M., et al., *DREAM is a Ca2+-regulated transcriptional repressor*. Nature, 1999. 398(6722): p. 80-4.
97. Hendricks, K. B., et al., *Yeast homologue of neuronal frequenin is a regulator of phosphatidylinositol-4-OH kinase*. Nature cell biology, 1999. 1(4): p. 234-41.
98. Rajebhosale, M., et al., *Phosphatidylinositol 4-OH kinase is a downstream target of neuronal calcium sensor-1 in enhancing exocytosis in neuroendocrine cells*. The Journal of biological chemistry, 2003. 278(8): p. 6075-84.
99. Zheng, Q., et al., *Neuronal calcium sensor-1 facilitates neuronal exocytosis through phosphatidylinositol 4-kinase*. Journal of neurochemistry, 2005. 92(3): p. 442-51.
100. Lin, L., et al., *Functional analysis of calcium-binding EF-hand motifs' of visinin-like protein-1*. Biochemical and biophysical research communications, 2002. 296(4): p. 827-32.
101. Spilker, C., T. Dresbach, and K. H. Braunewell, *Reversible translocation and activity-dependent localization of the calcium-myristoyl switch protein VILIP-1 to different membrane compartments in living hippocampal neurons*. The Journal of neuroscience: the official journal of the Society for Neuroscience, 2002. 22(17): p. 7331-9.
102. Boekhoff, I., et al., *The calcium-binding protein VILIP in olfactory neurons: regulation of second messenger signaling*. European journal of cell biology, 1997. 72(2): p. 151-8.
103. Brackmann, M., et al., *Neuronal Ca2+ sensor protein VILIP-1 affects cGMP signalling of guanylyl cyclase B by regulating clathrin-dependent receptor recycling in hippocampal neurons*. Journal of cell science, 2005. 118(Pt 11): p. 2495-505.
104. Braunewell, K. H., et al., *Intracellular neuronal calcium sensor (NCS) protein VILIP-1 modulates cGMP signalling pathways in transfected neural cells and cerebellar granule neurones*. Journal of neurochemistry, 2001. 78(6): p. 1277-86.
105. Braunewell, K. H. and E. D. Gundelfinger, *Intracellular neuronal calcium sensor proteins: a family of EF-hand calcium-binding proteins in search of a function*. Cell and tissue research, 1999. 295(1): p. 1-12.
106. Mahloogi, H., et al., *Overexpression of the calcium sensor visinin-like protein-1 leads to a cAMP-mediated decrease of in vivo and in vitro growth and invasiveness of squamous cell carcinoma cells*. Cancer research, 2003. 63(16): p. 4997-5004.
107. Dai, F. F., et al., *The neuronal Ca2+ sensor protein visinin-like protein-1 is expressed in pancreatic islets and regulates insulin secretion*. The Journal of biological chemistry, 2006. 281(31): p. 21942-53.
108. Bernstein, H. G., et al., *Regional and cellular distribution of neural visinin-like protein immunoreactivities (VILIP-1 and VILIP-3) in human brain*. Journal of neurocytology, 1999. 28(8): p. 655-62.
109. Laterza, O. F., et al., *Identification of novel brain biomarkers*. Clinical chemistry, 2006. 52(9): p. 1713-21.
110. Tarawneh, R., et al., *Visinin-like protein-1: diagnostic and prognostic biomarker in Alzheimer disease*. Annals of neurology, 2011. 70(2): p. 274-85.
111. Longa, E. Z., et al., *Reversible middle cerebral artery occlusion without craniectomy in rats*. Stroke, 1989. 20(1): p. 84-91.

112. Scheff, S. W., et al., *Morris water maze deficits in rats following traumatic brain injury: lateral controlled cortical impact.* Journal of neurotrauma, 1997. 14(9): p. 615-27.

113. Pettigrew, L. C., et al., *Focal cerebral ischemia in the TNFalpha-transgenic rat.* J Neuroinflammation, 2008. 5: p. 47.

114. Longa, E. Z., et al., *Reversible middle cerebral artery occlusion without craniotomy in rats.* Stroke, 1989. 20: p. 8.

115. Dubal, D. B., et al., *Estradiol protects against ischemic injury.* J Cereb Blood Flow Metab, 1998. 18(11): p. 1253-8.

What is claimed is:

1. A lateral flow device for detecting a presence of VILIP-1 protein in a biological sample, comprising:
    a sample portion for receiving the biological sample, wherein the sample portion removes red blood cells;
    a conjugate portion downstream of the sample portion that includes a conjugate, the conjugate including a first antibody conjugated to a detection probe, wherein the first antibody is selective for a first portion of VILIP-1, wherein the first portion is not a C-terminal portion of VILIP-1; and,
    a detection portion downstream of the conjugate portion that includes a second antibody that is selective for a second portion of VILIP-1, wherein the second portion is a C-terminal portion of VILIP-1.

2. The device of claim 1, wherein the sample portion further comprises a buffer solution.

3. The device of claim 1, wherein the detection probe is selected from a fluorescent compound, radioactive compound, a visual label, nanobeads and combinations thereof.

4. The device of claim 1, wherein the sample portion comprises a material for removing red blood cells selected from the group consisting of: asymmetric polysulfone, glass fiber filter, or unsaturated aliphatic fatty acid or ester thereof.

5. The device of claim 3, wherein the nanobeads are nanogold beads.

6. The device of claim 1, wherein the detection zone further comprises a control zone comprising a third antibody selective for the first antibody.

7. The device of claim 1, wherein the second or third antibody are immobilized in the detection zone as a stripe at a concentration of 4 µg/cm.

8. The device of claim 1, wherein the antibodies of the conjugate zone are immobilized on a conjugate pad.

9. The device of claim 1, wherein the detection zone comprises a nitrocellulose membrane.

10. The device of claim 1, further comprising a wicking portion.

11. The device of claim 1, wherein the first anti-VILIP-1 antibody associated with a detection probe is deposited with one or more supporting substances.

12. A method of detecting VILIP-1 protein in a biological sample, comprising
    providing a biological sample to a sample portion upstream of a conjugation zone of a separation membrane, wherein the sample portion removes red blood cells from the biological sample and wherein the conjugation zone comprises a first antibody selective for a non C-terminal portion of VILIP-1 associated with a detection probe immobilized thereon such that the VILIP-1 protein, if present in the biological sample, form a first antibody and VILIP-1 complex; and
    migrating the first antibody and VILIP-1 complex along the separation membrane to a detection zone comprising a second antibody selective for a C-terminal portion of VILIP-1 immobilized thereon, wherein the second anti-VILIP-1 antibody captures the first antibody and VILIP-1 complex resulting in detectable signals indicative of the presence and/or amount of the VILIP-1 protein in the biological sample.

13. The method of claim 12, wherein the detectable signals occur within a period of time less than 15 minutes from providing the biological sample to the separation membrane.

14. The method of claim 12, wherein the biological sample is a blood sample, a serum sample, or a plasma sample.

15. The method of claim 12, wherein the biological sample is 10 µl or less in volume.

16. The method of claim 12, wherein the sample portion comprises a material for removing red blood cells selected from the group consisting of: asymmetric polysulfone, glass fiber filter, or unsaturated aliphatic fatty acid or ester thereof.

17. The method of claim 12, wherein the biological sample is obtained from a subject suspected of suffering a brain injury or trauma.

18. The method of claim 17, wherein the biological sample is obtained from the subject within 60 minutes after suspected brain injury or trauma.

19. The method of claim 17, wherein the brain injury or trauma is neuronal damage, hypoxic damage or combinations thereof.

20. The method of claim 17, wherein the subject is a premature infant.

21. The method of claim 17, wherein the brain injury or trauma is stroke.

22. The method of claim 21, wherein the stroke is hemorrhagic or ischemic.

23. The method of claim 17, wherein the brain injury or trauma is traumatic brain injury (TBI).

24. The method of claim 23, wherein based on the concentration of VILIP-1 protein the TBI can be diagnosed as mild, medium or severe.

25. The method of claim 12, wherein the concentration of the VILIP-1 protein in the biological sample is less than 500 ng/ml.

26. The method of claim 12, wherein the detection probe may be selected from the group comprising fluorescent compounds, radioactive compounds, nanobeads, visual labels, or combinations thereof.

27. The method of claim 26, wherein the nanobeads are nanogold beads.

28. The device of claim 1, wherein one or both of the first portion and the second portion is or comprises a conformation of VILIP-1.

29. The device of claim 1, wherein the first portion is that recognized by antibody PL-A2 and/or the second portion is that recognized by antibody K-25.

30. The device of claim 1, wherein the first antibody is or comprises PL-A2 and or wherein the second antibody is or comprises K-25.

31. The method of claim 12, wherein one or both of the first portion and the second portion is or comprises a conformation of VILIP-1.

32. The method of claim 12, wherein the first portion is that recognized by antibody PL-A2 and/or the second portion is that recognized by antibody K-25.

33. The method of claim 12, wherein the first antibody is or comprises PL-A2 and or wherein the second antibody is or comprises K-25.

* * * * *